US007975564B2

(12) United States Patent
Ulevicius et al.

(10) Patent No.: US 7,975,564 B2
(45) Date of Patent: Jul. 12, 2011

(54) METHOD AND APPARATUS FOR INCREASING THE SIZE OF SMALL PARTICLES

(75) Inventors: Vidmantas Ulevicius, Vilnius (LT); Markku Kulmala, Helsinki (FI); Genrik Mordas, Vilnius (LT); Vytautas Matulevicius, Vilnius (LT); Vytautas Grigoraitis, Vilnius (LT); Kaarle Hämeri, Espoo (FI); Pasi Aalto, Helsinki (FI)

(73) Assignee: Dekati Oy, Tampere (FI)

( * ) Notice: Subject to any disclaimer, the term of this patent is extended or adjusted under 35 U.S.C. 154(b) by 732 days.

(21) Appl. No.: 10/585,509

(22) PCT Filed: Dec. 22, 2004

(86) PCT No.: PCT/FI2004/050192

§ 371 (c)(1),
(2), (4) Date: Oct. 14, 2008

(87) PCT Pub. No.: WO2005/066610

PCT Pub. Date: Jul. 21, 2005

(65) Prior Publication Data

US 2009/0031828 A1 Feb. 5, 2009

(30) Foreign Application Priority Data

Jan. 8, 2004 (FI) .................................. 20045003 U

(51) Int. Cl.
*G01N 1/00* (2006.01)

(52) U.S. Cl. ........................................................ 73/863

(58) Field of Classification Search ..................... 73/863
See application file for complete search history.

(56) References Cited

U.S. PATENT DOCUMENTS

| | | | | |
|---|---|---|---|---|
| 4,473,185 | A | 9/1984 | Peterson et al. | |
| 5,669,388 | A | 9/1997 | Vilkomerson | |
| 7,201,875 | B2 * | 4/2007 | Norton et al. | 422/73 |
| 2004/0062685 | A1 * | 4/2004 | Norton et al. | 422/81 |

FOREIGN PATENT DOCUMENTS

WO WO 99/41585 A2 8/1999

* cited by examiner

*Primary Examiner* — Hezron Williams
*Assistant Examiner* — Rodney T Frank
(74) *Attorney, Agent, or Firm* — Venable LLP; Eric J. Franklin

(57) ABSTRACT

A method and apparatus for increasing the size of small particles for a condensation particle counter, in which method a particle containing aerosol flow is divided into a sample flow and a sheath flow. The sheath flow is filtered, saturated with vapor and formed to a vortex flow in a saturator which vortex-flow continues in a condenser. The sample flow is introduced to the center of the vortex flow of the saturated sheath flow in the condenser for causing the vapor in the saturated sheath flow to condense on the particles in the sample flow thus increasing the size of the particles.

21 Claims, 3 Drawing Sheets

Prior art

METHOD AND APPARATUS FOR INCREASING THE SIZE OF SMALL PARTICLES

CROSS-REFERENCE TO RELATED APPLICATIONS

This application claims priority to Finnish patent application 20045003 filed 8 Jan. 2004 and is the national phase under 35 U.S.C. §371 of PCT/FI2004/050192 filed 22 Dec. 2004.

FIELD OF THE INVENTION

The invention relates to a method for increasing the particle size of small particles for a condensation particle counter. The invention also relates to an apparatus for implementing the method.

BACKGROUND OF THE INVENTION

Aerosols, that is, suspensions of fine particles in air or gas, are today recognized to play a central role in diverse environmental problems such as climate change, impaired visibility caused by the particles in the atmosphere and eutrofication of unhabited lands. They also have an effect to respiratory diseases. Aerosols are also the sites on which heterogeneous reactions of gaseous trace constituents occur. The sources of each of the major chemical constituents of the aerosols must be known and their role in atmospheric processes must be elucidated, in order to regulate and reduce their detrimental effects. There are indications that most of the mass in the fine aerosols (Dp.<2.5 μm) is secondary, i.e. is not directly emitted, but formed from gaseous precursors in the atmosphere. The absence of reliable aerosol data prevents understanding of the formation of these secondary aerosols and evaluation of their treatment in chemical transport models. However, legislation will soon be needed to consider the sources and contributions of the major individual aerosol components to the total mass in order to develop efficient abatement strategies for preventing climate change.

Detection and analysis of aerosols using a condensation particle counters (CPC), often known as condensation nucleus counters (CNC) is well known. CPC is used for example to detect small particles in aerosols, for example for outdoor and indoor air-quality research, filter and air cleaner research, particle formation and growth studies and combustion and engine-exhaust studies. The CPC is also used as the primary detection for obtaining particle size distributions, for example in scanning mobility particle sizers. With CPC it is possible to detect particles as small as 3 nm in diameter. CPC detects particles by condensing a vapor on the particles to grow them to large enough size that they can be counted e.g. optically or by other means. The measurement usually involves four steps: 1) the production of sufficient quantities of vapor, 2) creation of supersaturation necessary to activate the particles, 3) maintenance of the particles in the supersaturated state long enough to grow them to a detectable size and 4) detection of the grown particles. In a CPC, the aerosol is first saturated with a vapor and subsequently cooled to induce the supersaturation conditions. For a given saturation ration, the vapor can condense onto particles only if they are large enough. The minimum particle size capable of acting as a condensation nucleus is called the Kelvin diameter. The relationship between the supersaturation rate and Kelvin diameter ($d_p$) can be expressed as the following function [Tang 1976, Friedlander 1977]:

$$\frac{P_d}{P_s} = \delta m_f \exp\left(\frac{4v\gamma}{RTd_p}\right)$$

Where:

$p_d$ is the saturation vapor pressure on particle surface
$p_s$ is the equilibrium saturation vapor pressure
$\delta$ is activity coefficient
$m_f$ is mole fraction of the solute
$\gamma$ is the surface tension of the liquid
$v$ is the molar volume of the liquid
R is the gas constant and
T is the temperature.

Equation is derived for vapor condensed on a liquid droplets of the same material or on insoluble particles with wettable surface properties for the working fluid.

FIG. 1 shows a CPC according to prior art, which is a so-called cooling-type CPC. In this example, the vapor needed for particle growing is produced through cleaning and supersaturation from aerosol gas itself, and it is called here the sheath flow. In other words, the sheath flow is filtered aerosol flow, i.e. it contains the same gas mixture as the sample flow, without solid particles. The main parts of the CPC are a flow divider 5, saturator 1, condenser 2 and detector 7. The flow divider 5 divides the aerosol flow to sheath flow and sample flow. Saturator 1 has two sections which are integrated together: a saturating section 1*a*, which is a heated tube, with liquid impregnated felt lining, where the sheath flow becomes saturated with vapor, and a heated section 1*b*, without felt lining. In the condenser 2, the vapors condense on the particles contained in the sample flow, thus enlarging them to become big enough to be detected by an optical detector 7. The condenser 2 is cooled to a temperature lower than the temperature of the saturator 1.

The flow divider 5 comprises two channels, for example pipes or the like, an inner channel 5*a* and an outer channel 5*b*, which are set within each other. The inner channel 5*a* is attached at it's other end to channel 4 for taking in the aerosol flow and it's other end extends inside the saturator heated section 1*b*. The outer channel 5*b* forms the outer surface of the flow divider 5 and it is dosed from the top, that is, from the end inside the saturator heated section 1*b*, with a cover or the like, the center of which cover is permeated by a sample flow capillary 3.

The intaken aerosol flow flows upwards in inner channel 5*a*. The inner channel 5*a* ends at a distance from the cover, thus forming a slit 8 between the upper edge of the wall of the inner channel 5*a* and the cover. Part of the aerosol flow in the inner channel 5*a* enters through the slit to the space between the inner channel 5*a* and the outer channel 5*b* to form a sheath flow. The sheath flow is taken out from the flow divider 5 and led onwards for cleaning with filter 6. The filter 6 removes all particles from the sheath flow, after which the cleaned sheath flow is directed to a saturator 1. The flow divider ends to a sample flow capillary 3, which extends in to the saturator heated section 1*b*.

The sample flow, which has been separated from the aerosol flow by means of a sample flow capillary 3 attached to the flow divider 5, enters the cleaned and vapor saturated sheath flow in saturator heated part 1*b*, mixes with the saturated sheath flow and flows to the condenser 2. In the condenser 2, the vapors condense on the particles contained in the sample flow, thus enlarging them to become big enough to be detected by an optical detector 7 following the condenser 2.

However, there are several problems with the CPC according to FIG. 1. The detector responses are slow, and turbulent mixing of flows causes supersaturation fluctuations and fluctuations of cutsize both in saturator and in condenser. Another problem is that flow recirculations are created in the system. Thus, while some grown particles immediately exit the condenser and enter the detector, other particles just circulate inside the condenser and randomly exit at some later time, introducing an exponentially decaying distribution of delays between the time particle enters condenser and when it is detected. Thus it is impossible to obtain sensitive size distributions. Also due to long condenser which is needed for particle growth, the ultra small particles in the flow tend to hit the condenser walls, prior reaching the detector, thus causing erroneous results. Further problem is the long saturator and the large diameter of the felt tube in the saturation section 1*a*. This causes a laminar sheath flow in the felt tube of the saturation section 1*a*, resulting in a non-homogenous formation of vapor.

BRIEF DESCRIPTION OF THE INVENTION

The purpose of the present invention is thus to provide a method and an apparatus for increasing the size of small particles, which method and apparatus avoid the above-mentioned problems and by means of which the small particles in aerosol can be increased large enough to be detected with a detector, and substantially all particles are conveyed to the detector without any loss during conveyance.

The invention is based on the idea that the sample flow is introduced to the centre of with vapor saturated sheath flow. Prior to sample flow feeding point, the sheath flow is caused to form a vortex flow, that extends all the way from saturator to condenser and forms a shielding layer between the condenser wall and sample particles, thus preventing the sample particles hitting the walls and making it possible, that even the smallest particles will enter the detector. So there are no losses in the condenser.

In the apparatus according to the invention, the saturator and the condenser are integrated into one structure in such a manner that the measures of the apparatus, both the height and the width, are decreased and thus the flow delay times are shortened significantly. The condenser is formed in the same structure with the saturator, i.e. it is installed on top of the saturator, as its extension. The division of the aerosol to sheath flow and sample flow takes place in a flow divider, which is known as such from prior art. The cleaned sheath flow is brought to the lower part of the saturator tangentially, creating a turbulent vortex flow around the flow divider. The vortex flow helps the vapor saturation of the sheath flow, because it is in close contact with the liquid impregnated felt elements on the saturator inner lining. Further, because the structure formed by the saturator and the condenser is compact and short, the vortex-flow-effect created in the saturator continues to the condenser as the saturated sheath flow flows upwardly along the saturator and condenser inner surfaces. This means that there is a continuous supersaturated sheath flow upwards against the condenser walls as well. The particle-containing sample flow is introduced to the condenser to the centre of the vortex flow. Because the sample flow is confined near the centerline of the condenser, it encounters high supersaturation levels and negligible losses of the formed droplets to the wall. To assist the formation of the vortex in the condenser, it is possible to attach a vortex generating means in condenser, before the sample feeding point.

BRIEF DESCRIPTION OF THE DRAWINGS

In the following, the present invention will be described in more detail with reference to the appended figures, in which.

DETAILED DESCRIPTION OF THE INVENTION

Figure 1:
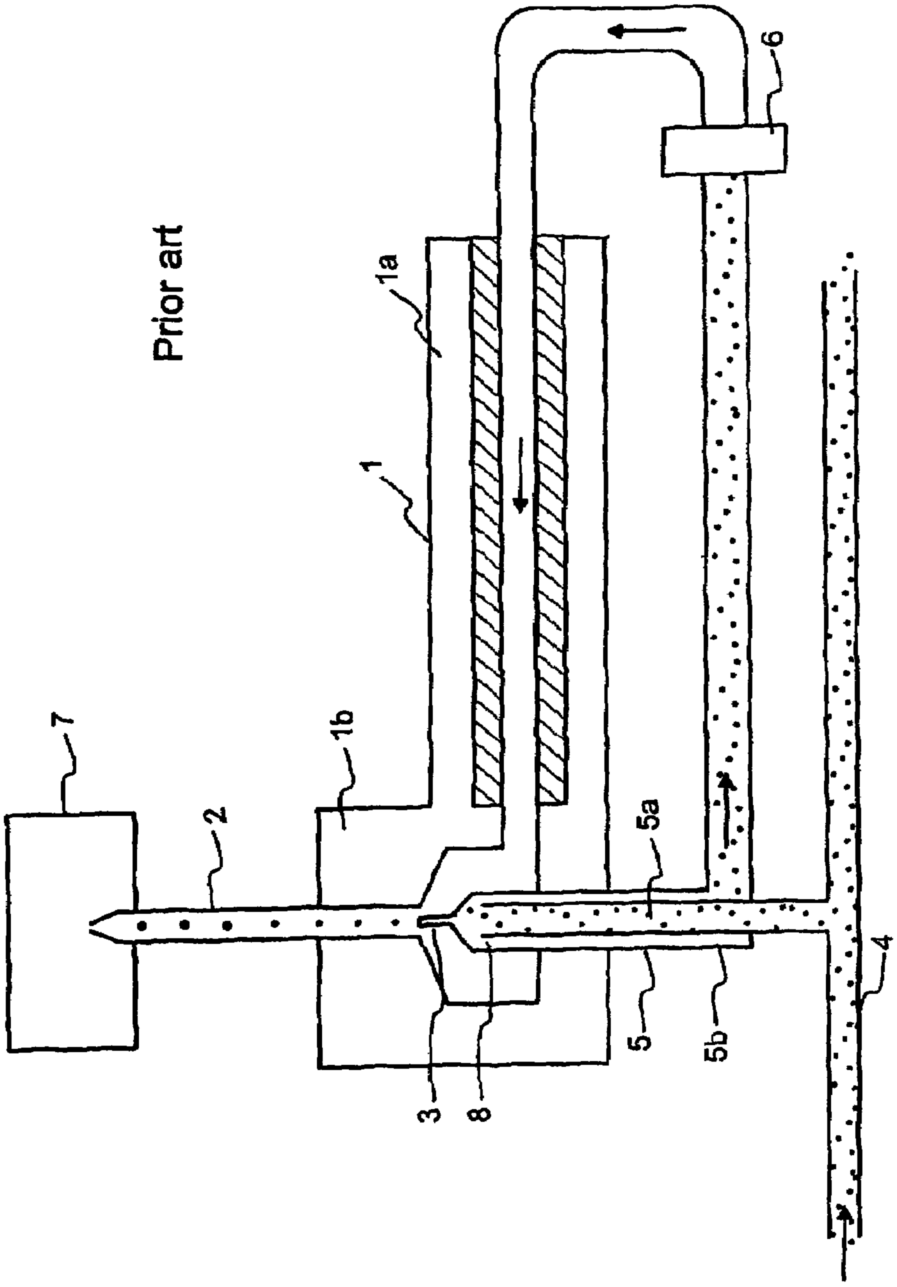
FIG. 1 shows schematically a CPC apparatus according to prior art.

FIG. 1 has been explained above, and thus it will not be discussed here any more.

Figure 2:
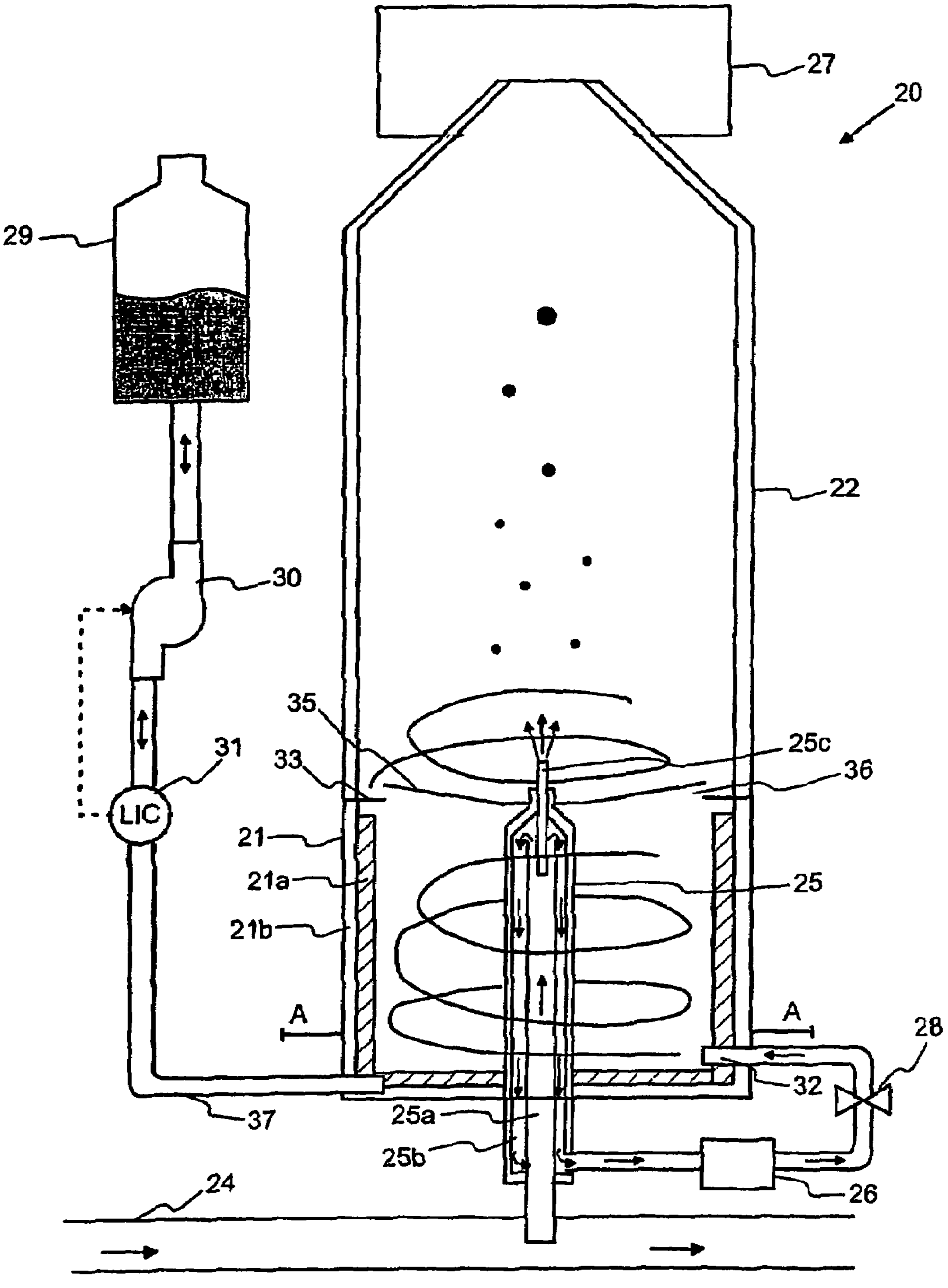
FIG. 2 shows schematically an apparatus for increasing the size of particles according to the present invention.

FIG. 2 shows a CPC apparatus 20, which includes an apparatus for increasing particles according to the invention. The aerosol flow is directed to the apparatus via a channel 24. The aerosol flow flows to a flow divider 25 via an inner channel 25*a*, whose other end extends inside the channel 24. The flow divider 25 and its operation is substantially the same as the flow divider 5 presented in connection with FIG. 1, which is why it will not be described in more detail in this context.

The flow divider 25 is placed inside a saturator 21, in the centre of it, so that the midpoint of the bottom of the saturator 21 and the longitudinal axis extending via the center of the cross section of the flow divider 25 are combined. The flow divider 25 extends through the height of the saturator 21 and it ends inside a condenser 22 mounted in connection with the saturator 21. The sheath flow divided in the flow divider 25 is filtered with a filter 26 and directed via a valve 28 and an input channel 32 to the saturator 21.

The saturator 21 is substantially cylindrical and it is placed in connection with a cylindrical condenser 21, below it, in such a manner that the center axes of the cylinders extending via the midpoints of the bottom of the above-mentioned cylinders are combined. Thus, the flow divider 25 is situated also in the centre of the condenser. Advantageously, the diameters of the outer surfaces of the saturator 21 and the condenser 22 are equal. The innersurface or the inner lining 21*a* of the saturator 21, including its bottom, is formed of a material, which is capable of absorbing and conveying liquid and holding as well as delivering moisture, i.e. it can be of a fabric, for example felt, porous material of rock or the like, or perforated expanded metal structure. The liquid introduced and absorbed to the inner lining 21*a* can be any liquid, for example water, alcohol or a mixture of them. Butanol is a liquid commonly used in the CPC for this purpose. The liquid is stored in a tank 29, from where it is fed by means of a peristaltic pump 30 and pipe 37 to the saturator, to its inner lining 21*a*.

The flow of the liquid used in the saturation from the tank 29 is controlled by means of the peristaltic pump 30 and a liquid surface controller 31. The controller 31 measures the level of the liquid surface in the pipe 37 and sends a control signal corresponding to the surface level (marked with a dashed line) to the pump 30. The measurement can be performed by any suitable measurement method, e.g. it can be an optical measurement. When the CPC 20 is not operating, the pump 30 operates to the other direction and removes the liquid accumulated in the saturator.

The outer surface 21*b* of the saturator 21, especially the surface against its inner lining 21*a*, is equipped with heating means (not shown in the figures), which heat the saturator 21, especially its inner lining 21*a*.

Figure 3:
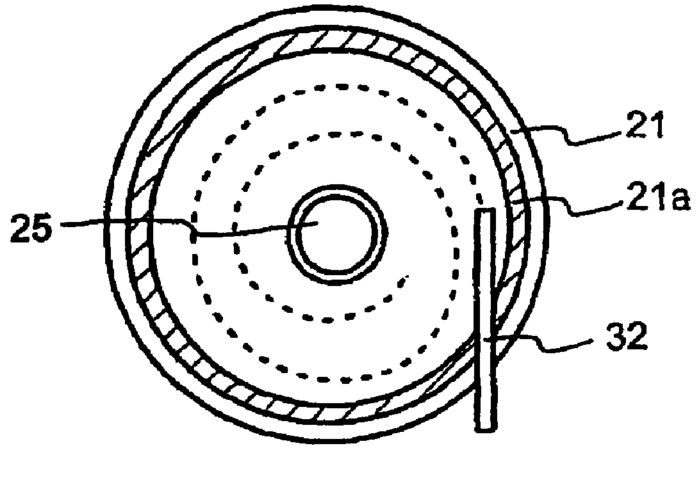
FIG. 3 shows the line A-A of the apparatus for increasing the size of particles shown in FIG. 2.

The sheath flow is fed to the saturator 21, to its lower part, via a feed pipe 32 tangentially in such a manner that a vortex flow is created inside the saturator 21. FIG. 3 shows a cross section along line A—A of the saturator, which illustrates the vortex formation. The feed pipe 32 is placed tangentially in relation to the saturator 21 in such a manner that the particle clean sheath flow fed to the saturator follows the inner lining 21*a* of the saturator and creates a vortex flow, i.e. spiral flow rising upwardly inside the saturator 21. Because the entire sheath flow is fed in the direction of the periphery of the saturator 21, the entire sheath flow gas flow comes into contact with the moist inner lining 21*a* of the saturator 21, and the saturation of the sheath flow is very effective. The created vortex flow dominates around the flow divider 25 and it extends over the entire length of the saturator 21, i.e. the sheath flow is in contact with the moist inner lining 21*a* of the saturator the entire time it is prevailing in the saturator 21. Consequently, the delay time of the sheath flow in the saturator 21 is longer and saturation degree of the sheath flow is higher than in a saturator known from the prior art.

From the saturator 21, the saturated sheath flow rises up to the condenser 22, which is placed above the saturator 21, as its extension. The condenser 22 is cooled by cooling its walls either from the outside of the condenser, for example with an external refrigerating medium, or the cooling is arranged inside the condenser, for example by means of a cooling gas flowing along the inner surfaces of the condenser.

The vortex flow of the sheath flow created in the saturator 21 continues in the condenser 22, now following the cooled inner walls of the condenser 22. Due to conservation of the flow's angular momentum, the swirl velocity of the vortex-flow increases near the center line of the condenser 22 thus creating an uniform supersaturation area in the central part of the condenser. Because the particles are introduced with the sample flow through the sample flow capillary 25*c* to the center of the condenser 22 and to the center of the vortex flow of the saturated sheath flow, they are carried upwardly and are easily supersaturated by this uniform supersaturation. The inward motion of the vortex-flow prevents the particles to hit the walls of the condenser and thus minimizes the losses. The grown particles are carried with the vortex flow in the condenser to the detector 27, which can be any detector suitable for particle counting, for example an optical counter.

Figure 4:
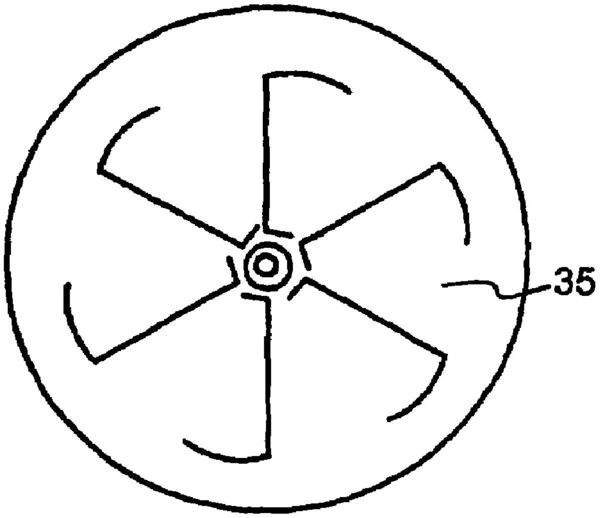
FIG. 4 shows a top view of a vortex generating means shown in FIG. 2.

In FIG. 2 are also shown vortex generating means in the condenser 22 for enhancing the vortex formation in the saturated sheath flow. The vortex generating means is e.g. a flow guide 35 having an outer edge 33, which outer edge encircles the condenser inner lining. The flow guide 35 and the outer edge 33 are connected together with sockets (not shown in the figure). The flow guide 35, shown in a top view in FIG. 4, is a circular, plate-like, possibly somewhat convex plate whose surface on the condenser 22 side has wing-like bended projections. The edges of the flow guide 35 extend over the outer edge 33, so that a gap 36 is formed between the outer edge and the flow guide through which gap the saturated sheath flow can flow into the condenser 22. The vortex generating means are placed in the bottom of the condenser 22, i.e. just above the saturator 21. The flow divider 25, which extends inside the condenser's lower part, narrows down in the saturator 21, just before condenser 22. The flow divider 25 with sample flow capillary 25*c* penetrates the flow guide 35 in the flow guide's center point.

The vortex generating means enhance the vortex flow of the saturated sheath flow discharged through the gap 36 to the condenser 22 thus minimizing the particle losses on the condenser walls and enhancing the supersaturation of the particles. The flow guide 35 can be a stationary plate-like member, acting as a flow vane or it can be a swirling plate, which is rotating around it's axis. Also it can be any other means, which is able to enhance the vortex flow of the saturated sheath flow.

The intention is not to restrict the invention to the embodiments described above by way of example, but it is intended that the invention can be interpreted widely within the scope of protection defined by the claims presented hereinbelow. Thus, the saturator 21 and the condenser 22 can be separate structures, which are attached to each other in an appropriate manner, or they can be integrated into a uniform structure. Also the vortex generating means in the condenser 22 are not essential for the working of the invention, but they can be used, when needed.

The invention claimed is:

1. A method for increasing the size of small particles for a condensation particle counter, the method comprising:
- dividing a particle containing aerosol flow into a sample flow and a sheath flow;
- filtering the sheath flow in order to remove particles contained in the sheath flow;
- saturating the filtered sheath flow with vapor;
- forming the sheath flow into a vortex flow; and
- introducing the sample flow to a center of the vortex-flow of the saturated sheath flow causing the vapor in the sheath flow to condense on the particles in the sample flow thus increasing the size of the particles.

2. The method according to claim 1, wherein the vortex flow is a spiral flow that flows upwardly along inner surfaces of a saturator and/or a condenser.

3. The method according to claim 1, wherein the sheath flow is formed to a vortex flow by feeding the sheath flow tangentially to a lower part of a saturator.

4. The method according to claim 1, wherein the sheath flow is saturated by forming the sheath flow into a vortex flow, which vortex flow flows along a moist inner lining of a saturator.

5. The method according to claim 1, wherein the vortex flow is formed to circulate around a flow divider.

6. The method according to claim 1, wherein the saturated sheath flow is brought to a vortex flow by a vortex generating means.

7. The method according to claim 6, wherein the vortex generating means includes a flow guide which is stationary or rotating.

8. The method according to claim 6, wherein the vortex flow has an inward motion, which keeps the particles in the sample flow in a center of a condenser.

9. The method according to claim 1, wherein the vortex flow is formed in a saturator and a condenser that are placed on top of each other.

10. The method according to claim 9, wherein the saturator and the condenser are cylindrical.

11. The method according to claim 1, wherein the sample flow is introduced to the center of the saturated sheath flow by a flow divider, that is situated in a center of a saturator and a condenser.

12. An apparatus for increasing the size of small particles for a condensation particle counter, the apparatus comprising:
- a flow divider for dividing an aerosol flow into a sample flow and a sheath flow;
- a filter for filtering the sheath flow;
- a saturator for saturating the filtered sheath flow with vapor, the saturator comprising means to form the sheath flow into a vortex flow; and a condenser, where the sample flow is introduced to the saturated sheath flow to condense the vapor in the sheath flow on the particles in the sample flow thus increasing a size of the particles, wherein the vortex flow formed in the saturator is arranged to continue in the condenser and the sample flow is arranged to be introduced to a center of the saturated sheath flow.

13. The apparatus according to claim 12, wherein the vortex flow is a spiral flow that is arranged to flow upwardly along inner surfaces of the saturator and/or the condenser.

14. The apparatus according to claim 12, wherein means to form the sheath flow to a vortex flow in the saturator comprises a pipe that is arranged tangentially to a lower part of the saturator.

15. The apparatus according to claim 12, wherein an inner lining of the saturator is moistened with liquid and wherein the sheath flow is arranged to be saturated by forming the sheath flow into a vortex flow arranged to flow along the moisted inner lining of the saturator.

16. The apparatus according to claim 12, wherein the condenser comprises a vortex generator operative to form the vortex flow of the saturated sheath flow.

17. The apparatus according to claim 16, wherein the vortex generator comprises a stationary or a rotating flow guide.

18. The apparatus according to claim 12, wherein the saturator and the condenser are placed on top of each other.

19. The apparatus according to claim 18, wherein the saturator and the condenser are cylindrical.

20. The apparatus according to claim 12, wherein the flow divider is arranged in a center of the saturator and the condenser and wherein the flow divider extends through a height of the saturator and ends inside the condenser.

21. The apparatus according to claim 12, wherein the flow divider comprises a sample flow capillary operative to feed the sample flow to the condenser to the center of the saturated sheath flow.

* * * * *